(12) United States Patent
Malinge

(10) Patent No.: US 6,790,654 B2
(45) Date of Patent: Sep. 14, 2004

(54) CELL CULTURE HARVESTING

(75) Inventor: David Serge Malinge, Hertfordshire (GB)

(73) Assignee: The Automation Partnership (Cambridge) Ltd., Hertfordshire (GB)

( * ) Notice: Subject to any disclaimer, the term of this patent is extended or adjusted under 35 U.S.C. 154(b) by 0 days.

(21) Appl. No.: 10/235,862

(22) Filed: Sep. 6, 2002

(65) Prior Publication Data

US 2003/0068814 A1 Apr. 10, 2003

(51) Int. Cl.[7] ............................................. C12M 1/14
(52) U.S. Cl. ......................... 435/299.2; 435/304.1; 435/308.1; 435/309.2; 15/211; 15/220.2
(58) Field of Search ..................... 435/283.1, 299.2, 435/304.1, 308.1, 309.2, 378, 379, 395; 128/757; 15/211, 220.2

(56) References Cited

U.S. PATENT DOCUMENTS

| | | | |
|---|---|---|---|
| 4,144,091 A | * | 3/1979 | Tran .............................. 134/6 |
| 4,810,652 A | * | 3/1989 | Witt ......................... 435/308.1 |
| 5,900,374 A | | 5/1999 | Otto-Nagels ................ 435/379 |
| 6,194,199 B1 | * | 2/2001 | Asa ......................... 435/309.1 |

* cited by examiner

Primary Examiner—David A. Redding
(74) Attorney, Agent, or Firm—Dykema Gossett PLLC

(57) ABSTRACT

A scraper for scraping live cells from a substrate. The scraper comprises a magnetic core and an elastomeric housing surrounding at least a portion of the magnetic core and defining at least one scraping blade. A method of scraping and a system for scraping are also provided.

5 Claims, 2 Drawing Sheets

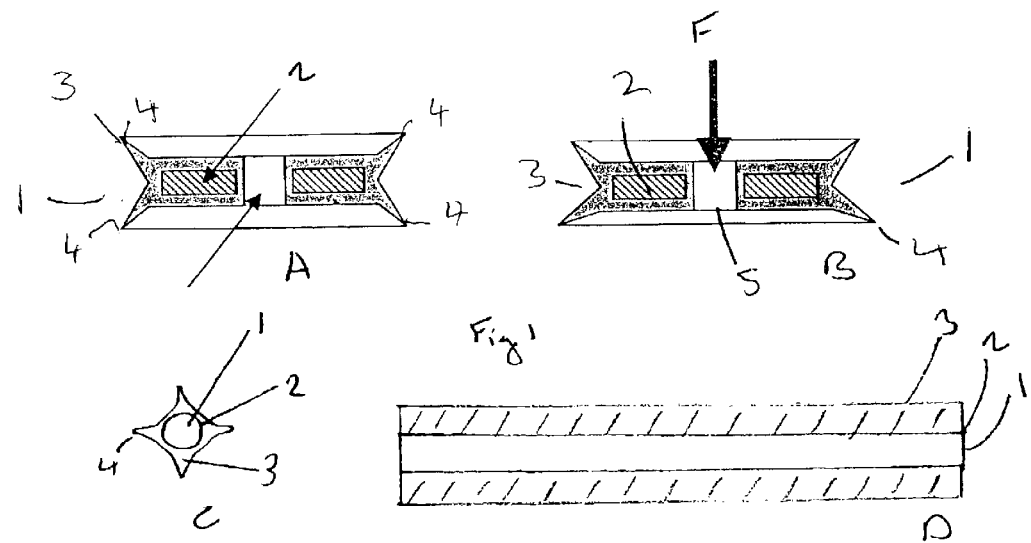
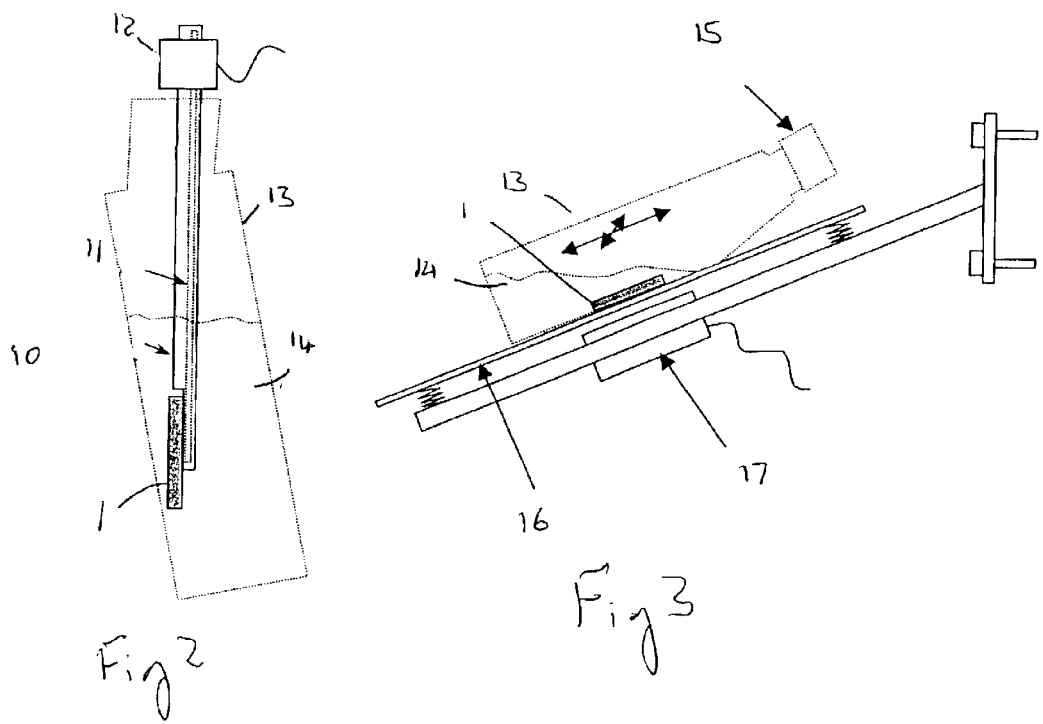

CELL CULTURE HARVESTING

This invention relates to the growth of cell cultures and the harvesting thereof.

There are many biochemical and chemical analyses for which it is necessary to have a source of live cells. The culture of such live cells, is however, time consuming and has traditionally been carried out by hand, making it extremely labour intensive. The traditional approach has been to attempt to grow the necessary live cells on a substrate in a source of food for the cells, which is normally a liquid solution of various chemicals. The most common approach has been to grow the cells on the interior surface of a flask which can contain the necessary solution. However, the harvesting of the cell culture from the inner surface of the flask is time consuming and awkward because of the need to gain access through what is generally a narrow flask opening and also and also in view of the need to remove the cells from the surface in such a way that minimal damage occurs to them. In practice this has normally therefore required the expertise of a skilled technician. Furthermore, it has resulted in an operation employing some form of scraping implement, which can lead to repetitive strain injuries for the technician. Also, various other stages in biochemical and chemical analyses have been automated, the need for increased volumes of live cell culture has increased. Accordingly, there is a desire to automate the process of cell cultures, and the harvesting of live cell cultures. However, in view of the awkward nature of the scraping of such cell cultures and the need for the performance of complex precision manoeuvres in order to harvest the cell cultures, automation of harvesting has been particularly difficult to achieve.

The present invention seeks to provide an apparatus and method for improving the harvesting of live cell cultures either manually or automatically.

According to the present invention there is provided a scraper for scraping live cells from a substrate, the scraper comprising:

a core formed from magnetizable material; and an elastomeric housing surrounding at least a portion of the magnetic core and defining at least one scraping blade.

The housing may totally encase the magnetic core. The scraper may have a hole formed in its centre. The housing may define plural scraping blades and may have a symmetrical cross-section.

According to the present invention there is also provided a system for scraping live cells from a substrate, the system comprising:

a scraper of the type defined above;

an magnetic or electromagnetic holder for holding the scraper when not in use; and a magnetic force generator for generating, in use, a magnetic force that can be applied to the scraper in use to generate relative movement between the scraper and the substrate.

The holder may comprise a holding rod with a soft magnetic core and an electromagnet coil associated therewith. It may be shaped so that it can pass, together with the scraper, through the neck of a flask, the inner surface of which defines the substrate.

The magnetic force generator may be an electromagnet and may have means associated therewith for controlling the force applied to the scraper. This force controlling means may include means for controlling the separation between the scraper and the magnetic force generator in use. The magnetic force generator may also comprise means for generating movement between the substrate and the scraper.

The provision of the magnetic scraper according to the invention enables simple and effective scraping to be performed without the need for performance of a skilled operation by a human operator. It also provides a method of harvesting live cells which can increase the efficiency of harvesting and allow total automation of the harvesting process.

An example of the present invention will now be described with reference to the accompanying drawings in which:

FIG. 1 is a series of schematic views of example scrapers according to the invention;

FIG. 2 is a side schematic view of a scraper according to the invention retained on a holder;

FIG. 3 is a side schematic view of the scraper of the invention and associated control equipment in use.

Figure 4:
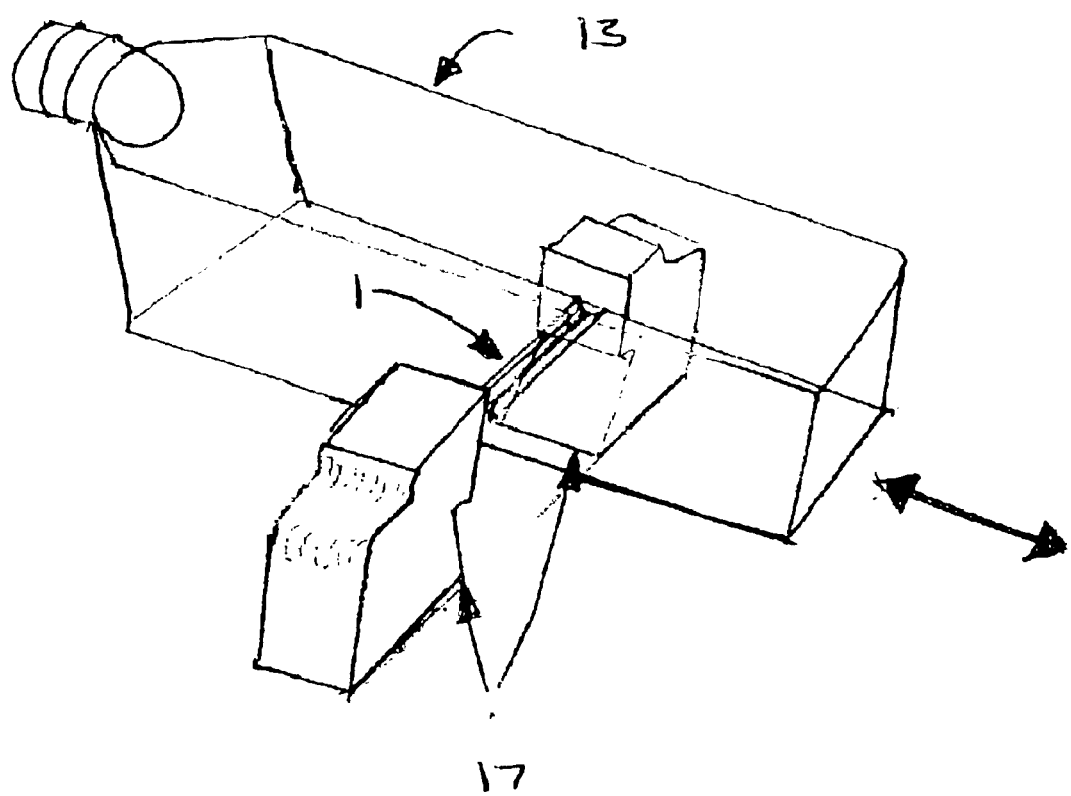
FIG. 4 is a side schematic view of alternative scraping control equipment.

Referring to FIGS. 1A and 1B, a scraper 1 has a magnetisable metal core 2, attached to which is a casing 3 formed from an elastomer, such as polypropylene or other plastics material. The casing 3 is shaped so as to define, in this example, two scraping blades 4. It is not essential to have two blades, but as will be appreciated from the description below, this gives the scraper 1 a symmetry so that its orientation in use is of less concern during control of the scraper 1. In this example the magnetic core 2 is formed from steel and is a simple rectangular or circular washer with a central hole 5 which can allow liquid to pass through the scraper 1 in use. It will be appreciated that if the scraper is elongate there may only be two scraping surfaces on either side of the scraper 1.

FIG. 1B shows the scraper 1 when it is deformed in use by the application of a magnetic force on it, so that some of the scraping surfaces 4 of the casing 3 deform and engage with a surface (not shown) from which cell cultures are to be scraped in use.

FIGS. 1C and 1D show end and side cross-sectional views of a second example scraper according to the invention, in which components corresponding to those of FIGS. 1A and 1B are numbered identically. In this case the scraper 1 has an elongate core 2 surrounded by a casing 3 which defines for scraping blades 4.

The method of the invention, together with the operation of the scraper 1 of FIG. 1 will now be described with reference to FIGS. 2 and 3. These figures show an automated system and method, but the underlying principles of the invention could be employed manually by an operator. FIG. 2 shows the scraper 1 releasably held by a retaining member 10 which forms an electromagnet with a soft magnetic material 11 at its core and an associated coil 12. In use a flask 13, which contain cell culturing fluid 14 is placed over the scraper 1 and retaining member 10 by automated machinery (not shown). At this stage the coil 12 is deactivated such that the scraper 1 can fall into the flask 13, which can then be removed from the retaining member 10.

As an alternative, the retaining member 10 may be formed from a magnetic material and the scraper 1 removed therefrom by engaging one end of the scraper 1 with the neck of the flask 13, the flask 13 and retaining member 10 then being removed with respect to one another to draw the scraper 1 out of engagement with the holder 10 so that the flask 13 can then be moved. After this, if necessary a cap 15 is then placed on the flask 13 and the flask 13, together with the scraper 1 and fluid 14 is placed at an inclined position on a support 16, as shown in FIG. 3. Positioned on the opposite side of the base 16 to the flask 13 is a magnet or electromagnet 17 which attracts the scraper 1. The flask 13 can then be moved with respect to the magnet 17 either by movement of the base 16, the magnet 17, or the flask 13 itself. This action moves the scraper 1 across the inner surface of the flask 13 to remove cell cultures that are formed therein so that they float in the fluid 14.

The force applied by the scraper 1 can be controlled by either controlling the level of the magnetic field generated by the magnet or electromagnet 17 or by controlling the spacing of the flask 13 from the magnet or electromagnet 17 by movement of the base 16 to increase or reduce the spacing between the scraper 1 and the magnet or electromagnet 17 or both.

Once the scraper 1 has been moved over as much of the inner surface of the flask 13 as is necessary (this may, include inversion of the flask 13 about its longitudinal axis), followed by further scraping, the flask 13 is moved back over the retaining member 10. The coil 12 can then be activated and the scraper 1 drawn out of the fluid and re-attached to the retaining member 10 so that the scraper 1 is then removed from the flask 13. The harvested cell culture in the solution 14 can then be moved for dispensing.

FIG. 4 shows an alternative scraping control mechanism in which permanent magnets 17 (or alternatively electromagnet 17) are shaped so that the flask 13 and scraper 1 contained therein can be positioned therebetween and relative movement between the flask 13 and the magnets 17 can be generated to move the scraper 1 with respect to the interior surface of the flask 13.

As will be appreciated from the above, the present invention provides a method of scraping the interior surfaces of cell culture flask 13 that is effective and which can be automated regardless of the shape of the flask itself. It also enables the provision of a scraping method which can have its scraping sources controlled to a considerable degree to ensure that no damage (or minimal damage) is caused to the cells that have been cultured during their removal. This increases cell harvest yields, improving the overall efficiency and cost effectiveness of the harvesting process.

What is claimed is:

1. A system for scraping live cells from a substrate, the system comprising:

a scraper;

a static magnet or electromagnetic holder for holding the scraper when not in use; and a magnetic force generator for generating, in use, a magnetic force that can be applied to the scraper in use to generate relative movement between the scraper and the substrate, and wherein the holder is shaped so that it can pass, together with the scraper, through the neck of a flask, the inner surface of which defines the substrate.

2. A system according to claim 1, wherein the holder comprises a holding rod with a soft magnetic core and an electromagnet coil associated therewith.

3. A substrate according to claim 1, wherein the magnetic force generator is an electromagnet.

4. A system according to claim 1, wherein the magnetic force generator has means associated therewith for controlling the force applied to the scraper.

5. A system according to claim 1, wherein the magnetic force generator comprises means for generating movement between the substrate and the scraper.

* * * * *